United States Patent
Yamaguchi

(10) Patent No.: US 9,097,589 B2
(45) Date of Patent: Aug. 4, 2015

(54) SIGNAL PROCESSING APPARATUS, SIGNAL PROCESSING METHOD AND COMPUTER READABLE MEDIUM

(75) Inventor: Hiroshi Yamaguchi, Kaisei-machi (JP)

(73) Assignee: FUJIFILM CORPORATION, Tokyo (JP)

( * ) Notice: Subject to any disclaimer, the term of this patent is extended or adjusted under 35 U.S.C. 154(b) by 522 days.

(21) Appl. No.: 12/385,207

(22) Filed: Apr. 1, 2009

(65) Prior Publication Data

US 2009/0252389 A1    Oct. 8, 2009

(30) Foreign Application Priority Data

Apr. 2, 2008    (JP) ................. 2008-095956

(51) Int. Cl.
- A61B 6/00 (2006.01)
- G06K 9/00 (2006.01)
- G01J 3/51 (2006.01)
- A61B 1/00 (2006.01)
- A61B 1/06 (2006.01)
- A61B 5/00 (2006.01)

(52) U.S. Cl.
CPC ............... *G01J 3/51* (2013.01); *A61B 1/00009* (2013.01); *A61B 1/0638* (2013.01); *A61B 5/0059* (2013.01); *A61B 5/0084* (2013.01); *G01J 3/513* (2013.01); *A61B 5/441* (2013.01)

(58) Field of Classification Search
CPC ............. A61B 1/00009; A61B 1/0638; A61B 5/0059; A61B 1/0084; A61B 5/441; G01J 3/51; G01J 3/513
See application file for complete search history.

(56) References Cited

U.S. PATENT DOCUMENTS

| 4,945,409 A | 7/1990 | Nakamura |
| 6,002,137 A * | 12/1999 | Hayashi ............ 250/458.1 |
| 6,032,070 A | 2/2000 | Flock et al. |

(Continued)

FOREIGN PATENT DOCUMENTS

| GB | 2 429 385 A | 2/2007 |
| GB | 2 429 523 A | 2/2007 |

(Continued)

OTHER PUBLICATIONS

English translation of JP 2002-272744 (Masanori, Publication date: Sep. 24, 2002) provided by IPDL translation tool.*

(Continued)

*Primary Examiner* — Katherine Fernandez
(74) *Attorney, Agent, or Firm* — McGinn IP Law Group, PLLC

(57) ABSTRACT

A signal processing apparatus includes an optical intensity detecting section that detects an intensity of light from a subject at a first wavelength and a second wavelength, where the first wavelength is different from the second wavelength, a pigment component identifying section that identifies a pigment component in the light from the subject, based on (i) a difference between a first absorptance of the subject at the first wavelength and a second absorptance of the subject at the second wavelength and (ii) a difference between the intensity at the first wavelength and the intensity at the second wavelength that are detected by the optical intensity detecting section, and an illumination light component identifying section that identifies an illumination light component in the light from the subject, based on a subject image obtained by image-capturing the subject and the pigment component identified by the pigment component identifying section.

14 Claims, 8 Drawing Sheets

(56) References Cited

U.S. PATENT DOCUMENTS

| | | | |
|---|---|---|---|
| 6,064,898 A * | 5/2000 | Aldrich | 600/316 |
| 6,272,374 B1 | 8/2001 | Flock et al. | |
| 6,293,911 B1 * | 9/2001 | Imaizumi et al. | 600/160 |
| 2001/0027273 A1 | 10/2001 | Flock et al. | |
| 2006/0276966 A1 | 12/2006 | Cotton et al. | |
| 2007/0161910 A1 * | 7/2007 | Preece et al. | 600/476 |

FOREIGN PATENT DOCUMENTS

| | | |
|---|---|---|
| JP | 2643941 B2 | 8/1997 |
| JP | 2001-037718 A | 2/2001 |
| JP | 2002-095635 | 4/2002 |
| JP | 2002-272744 | 9/2002 |
| JP | 2002-306458 | 10/2002 |
| WO | WO 96/39925 | 12/1996 |
| WO | WO 2004/010862 A2 | 2/2004 |

OTHER PUBLICATIONS

European Search Report dated Jul. 16, 2009.
Preece, et al., "Model-Based Parameter Recovery from Uncalibrated Optical Images", Medical Image Computing and Computer-Assisted Intervention—MIC CAI 2005 Lecture Notes in Computer Science: LNCS, Springer, Berlin, DE, vol. 3750, Jan. 1, 2005, pp. 509-516, XP019021797 ISBN: 978-3-540-29326-2.
European Search Report dated Aug. 2, 2010.
Japanese office action dated Sep. 18, 2012 with an English translation thereof.
Japanese Office Action dated May 7, 2013 with English translation.
European Office Action dated Mar. 6, 2014.

* cited by examiner

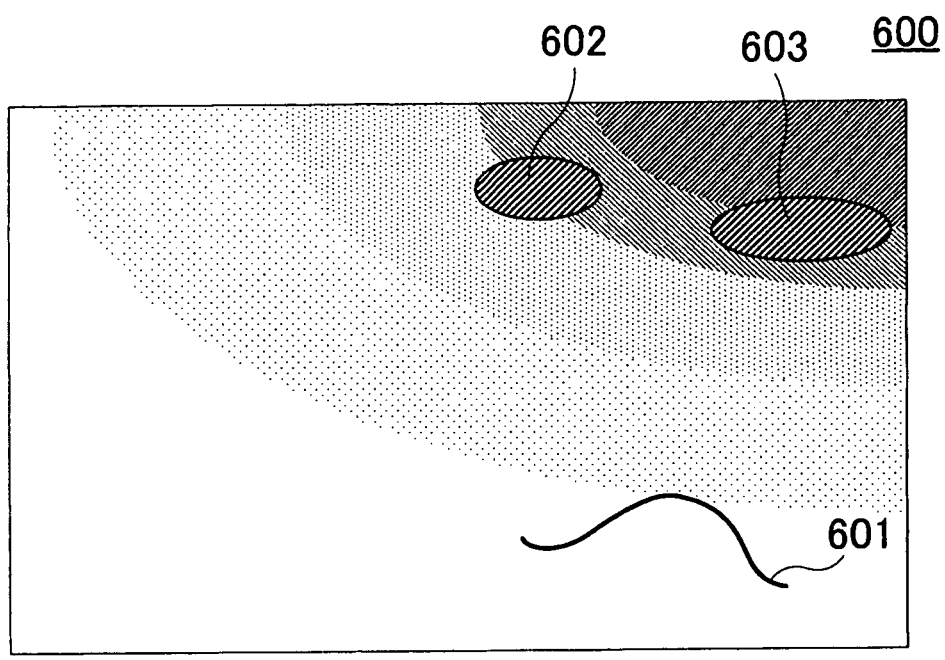
F I G . 6

US 9,097,589 B2

SIGNAL PROCESSING APPARATUS, SIGNAL PROCESSING METHOD AND COMPUTER READABLE MEDIUM

CROSS REFERENCE TO RELATED APPLICATION

The present application claims priority from a Japanese Patent Application No. 2008-095956 filed on Apr. 2, 2008, the contents of which are incorporated herein by reference.

BACKGROUND

1. Technical Field

The present invention relates to a signal processing apparatus, a signal processing method, and a computer readable medium storing thereon a program. More particularly, the present invention relates to a signal processing apparatus and a signal processing method for identifying an illumination light component in light received from a subject, and to a computer readable medium storing thereon a program for use with the signal processing apparatus.

2. Related Art

A technique is devised to generate an image signal without an illumination light reflection component by detecting a difference between two visual signals formed by light having two different wavelengths at which an observation target exhibits different light absorption characteristics, as disclosed, for example, in Japanese Patent No. 2643941. Another technique is devised to measure a concentration of a light absorbing substance in a blood without being affected by a change in oxygen saturation, by referring to a light attenuation ratio among a plurality of different wavelengths, as disclosed, for example, in Japanese Patent No. 3972176. Yet another technique is devised to generate a differential image representing a distribution of oxygenated hemoglobin by detecting a difference in two images formed by light of two different wavelengths for which oxygenated hemoglobin exhibits different light reflection characteristics, as disclosed, for example, in Japanese Patent Application Publication No. 2002-272744. Yet another technique is devised to capture a band image of a discrete spectral distribution of a subject by limiting a wavelength range of illumination light used to irradiate the subject, as disclosed, for example, in Japanese Patent Application Publication No. 2002-95635.

These techniques, however, are incapable of producing an image without influence of a pigment of a subject. An image of a living organism cannot be used to accurately judge a condition of an uneven shape such as a lesion of the surface of the living organism before influence of hemoglobin, which is a pigment of the living organism, is eliminated.

SUMMARY

Therefore, it is an object of an aspect of the innovations herein to provide a signal processing apparatus, a signal processing method and a computer readable medium, which are capable of overcoming the above drawbacks accompanying the related art. The above and other objects can be achieved by combinations described in the independent claims. The dependent claims define further advantageous and exemplary combinations of the innovations herein.

According to the first aspect related to the innovations herein, one exemplary signal processing apparatus may include a signal processing apparatus for separating light from a specified subject into an illumination light component and a pigment component, where the illumination light component results from a color of light with which the subject is irradiated, and the pigment component results from a color of a pigment of the subject. The signal processing apparatus includes an optical intensity detecting section that detects an intensity of the light from the subject at a first wavelength and a second wavelength, where the first wavelength is different from the second wavelength, a pigment component identifying section that identifies the pigment component in the light from the subject, based on (i) a difference between a first absorptance of the subject at the first wavelength and a second absorptance of the subject at the second wavelength and (ii) a difference between the intensity at the first wavelength and the intensity at the second wavelength that are detected by the optical intensity detecting section, and an illumination light component identifying section that identifies the illumination light component in the light from the subject, based on a subject image obtained by image-capturing the subject and the pigment component identified by the pigment component identifying section.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

BRIEF DESCRIPTION OF THE DRAWINGS

FIG. 6 illustrates an example of the subject image obtained by the subject image obtaining section 126.

DESCRIPTION OF EXEMPLARY EMBODIMENTS

Some aspects of the invention will now be described based on the embodiments, which do not intend to limit the scope of the present invention, but exemplify the invention. All of the features and the combinations thereof described in the embodiment are not necessarily essential to the invention.

Figure 1:
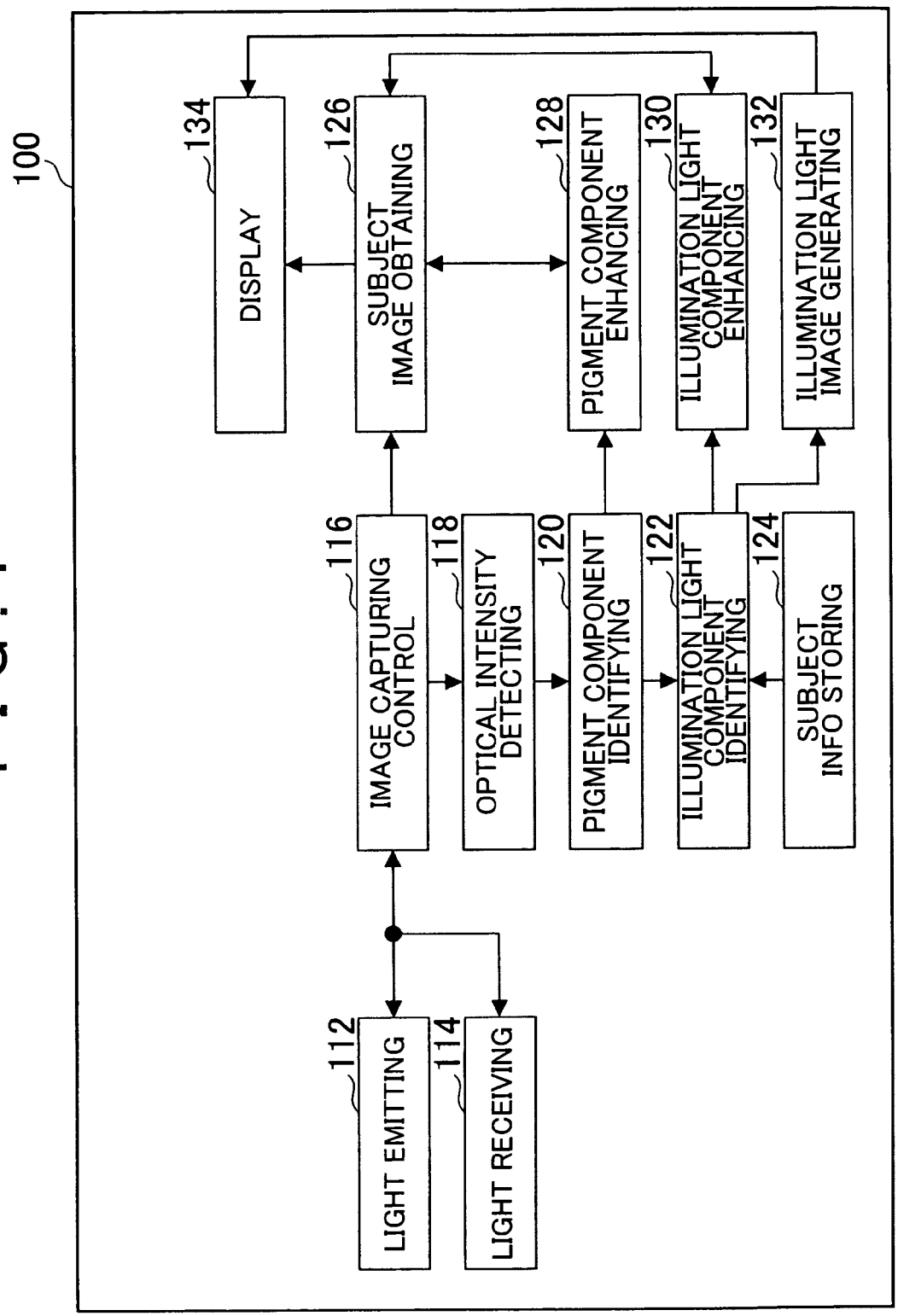
FIG. 1 illustrates an exemplary block configuration of an image capturing apparatus 100 relating to an embodiment of the present invention.

FIG. 1 illustrates an exemplary block configuration of an image capturing apparatus 100 relating to an embodiment of the present invention. The following description is made with an assumption that the image capturing apparatus 100 is an example of a signal processing apparatus.

The image capturing apparatus 100 separates light from a specified subject into an illumination light component and a pigment component. The illumination light component results from the color of light with which the subject is irradiated. The pigment component results from the color of a pigment of the subject. The illumination light component may be a surface reflection component, which is a component of the light reflected by the surface of the subject. In other words, the image capturing apparatus 100 may separate the light from the specified subject into the surface reflection component and the pigment component.

The image capturing apparatus 100 includes a light emitting section 112, a light receiving section 114, an image capturing control section 116, an optical intensity detecting section 118, a pigment component identifying section 120, an illumination light component identifying section 122, and a subject information storing section 124. Furthermore, the image capturing apparatus 100 includes a subject image obtaining section 126, a pigment component enhancing section 128, an illumination light component enhancing section 130, an illumination light image generating section 132, and a display section 134.

The image capturing apparatus 100 may be an endoscope. When the image capturing apparatus 100 is an endoscope, the light emitting section 112 and the light receiving section 114 may be provided in the end of an insert portion of the endoscope, which is to be inserted into a living organism. In a different example, the light emitting section 112 may be provided outside the insert portion and send light to the living organism through a light guide provided in the insert portion of the endoscope. The light receiving section 114 may be provided outside the insert portion and receive light from the living organism through the light guide provided in the insert portion of the endoscope.

The light emitting section 112 emits light to a subject. Specifically speaking, the light emitting section 112 emits light having a first wavelength at which the subject exhibits a minimal light absorption characteristic. For example, the light emitting section 112 emits, as an example of the light having the first wavelength, light having a wavelength of 440 nm at which hemoglobin exhibits a minimal light absorption characteristic. The light emitting section 112 also emits light having a second wavelength at which the subject exhibits a maximal light absorption characteristic. For example, the light emitting section 112 emits, as an example of the light having the second wavelength, light having a wavelength of 500 nm at which hemoglobin exhibits a maximal light absorption characteristic.

The light emitting section 112 may emit wideband light including the first and second wavelengths, which is used to detect the intensities of the light having the first wavelength and the light having the second wavelength. For example, the light emitting section 112 may emit white light, which is used to detect the intensities of the light having the first wavelength and the light having the second wavelength.

The light emitting section 112 may include a first light emitting element that emits the light having the first wavelength and a second light emitting element that emits the light of the second wavelength. The light emitting section 112 may include a first emission filter that transmits the first wavelength and a second emission filter that transmits the second wavelength.

The light emitting section 112 may further emit wideband light, which is used to capture a subject image. For example, the light emitting section 112 may further emit white light, which is used to capture a subject image.

The light receiving section 114 receives light from the subject. Specifically speaking, the light receiving section 114 receives light having the first wavelength and light having the second wavelength, which are used to detect the intensities of the light having the first wavelength and the light having the second wavelength. For example, the light receiving section 114 receives light having a wavelength of 440 nm and light having a wavelength of 500 nm, where the former is shown as an example of the light having the first wavelength and the latter is shown as an example of the light having the second wavelength, which are used to detect the intensities of the light having the first wavelength and the light having the second wavelength.

The light receiving section 114 may include a plurality of first light receiving elements for receiving the light having the first wavelength and a plurality of second light receiving elements for receiving the light having the second wavelength. In compliance with this configuration, the light receiving section 114 may include a plurality of first reception filters that mainly transmit the light having the first wavelength and a plurality of second reception filters that mainly transmit the light having the second wavelength. In place of the first and second light receiving elements, the light receiving section 114 may include a first light measuring section that detects the intensity of the light having the first wavelength and a second light measuring section that detects the intensity of the light having the second wavelength.

The light receiving section 114 may be a CCD or CMOS in which the first and second light receiving elements are regularly arranged. In a different example, the first light receiving elements may form a CCD or CMOS and the second light receiving elements may form a different CCD or CMOS.

The light receiving section 114 may further receive wideband light from the subject, which is used to capture a subject image. For example, the light receiving section 114 may further receive white light from the subject, which is used to capture a subject image.

The light receiving section 114 may further include a plurality of light receiving elements for receiving the wideband light from the subject, which is used to capture a subject image. The light receiving section 114 may further include a plurality of color-specific light receiving elements for receiving the respective color components of the wideband light from the subject, which is used to capture a subject image. For example, the light receiving section 114 may further include a plurality of color-specific light receiving elements for separately receiving the R, G and B components of the wideband light from the subject, which is used to capture a subject image.

The image capturing control section 116 controls the light emission timing of the light emitting section 112. For example, the image capturing control section 116 may control the light emitting section 112 to alternately emit the light having the first wavelength and the light having the second wavelength. The image capturing control section 116 may control the light emitting section 112 to simultaneously emit the light having the first wavelength and the light having the second wavelength.

The image capturing control section 116 may control the light emitting section 112 to sequentially emit the light having the first wavelength, the light having the second wavelength and the wideband light used to capture a subject image. When the light receiving section 114 can simultaneously receive the light having the first wavelength in the wideband light, the light having the second wavelength in the wideband light, and the wideband light used to capture a subject image, the image capturing control section 116 may control the light emitting section 112 to only emit the wideband light.

The image capturing control section 116 controls the light reception timing of the light receiving section 114. For example, the image capturing control section 116 may control the light receiving section 114 to alternately receive the light having the first wavelength and the light having the second wavelength. The image capturing control section 116 may control the light receiving section 114 to simultaneously receive the light having the first wavelength and the light having the second wavelength.

When the light emitting section 112 sequentially emits the light having the first wavelength, the light having the second wavelength, and the wideband light used to capture a subject image, the image capturing control section 116 may control the light receiving section 114 to sequentially receive the light having the first wavelength, the light having the second wavelength, and the wideband light used to capture a subject image. In this manner, the image capturing control section 116 may sequentially capture an image based on the light having the first wavelength, an image based on the light having the second wavelength, and the subject image.

On the other hand, when the light emitting section 112 only emits wideband light, the image capturing control section 116 may control the light receiving section 114 to simultaneously receive the light having the first wavelength in the wideband light, the light having the second wavelength in the wideband light, and the wideband light. In this manner, the image capturing control section 116 may simultaneously capture an image based on the light having the first wavelength, an image based on the light having the second wavelength, and the subject image.

The optical intensity detecting section 118 detects the intensities at the first and second wavelengths of the light from the subject. Specifically speaking, the optical intensity detecting section 118 detects the intensity at the first wavelength, at which the subject exhibits a minimal light absorption characteristic, and the intensity at the second wavelength, at which the subject exhibits a maximal absorption characteristic. The optical intensity detecting section 118 may detect the intensities of the light having the first wavelength and the light having the second wavelength that are respectively received by the light receiving section 114.

The subject information storing section 124 stores color information to identify the pigment component in the light from the subject. For example, the subject information storing section 124 may store color information of the subject in association with a first difference between a first absorptance and a second absorptance of the subject and a second difference between the intensity of the light having the first wavelength and the intensity of the light having the second wavelength, which are detected by the optical intensity detecting section 118. Here, the first absorptance indicates the absorptance of the subject for the light having the first wavelength, and the second absorptance indicates the absorptance of the subject for the light having the second wavelength.

The subject information storing section 124 may store color information defining the intensities of the respective color components. For example, the subject information storing section 124 may store color information indicating the intensities of the B, G and R components.

The pigment component identifying section 120 identifies the pigment component in the light from the subject, based on the first difference between the first absorptance and the second absorptance of the subject and the second difference between the intensity of the light having the first wavelength and the intensity of the light having the second wavelength, which are detected by the optical intensity detecting section 118. The pigment component identifying section 120 may identify the pigment component in the light from the subject, based on the color information stored in the subject information storing section 124. For example, the pigment component identifying section 120 may calculate the first difference and the second difference, and then obtain from the subject information storing section 124 the color information associated with the calculated first and second differences.

The pigment component identifying section 120 may use, as the first difference, the ratio between the first absorptance of the subject for the light having the first wavelength and the second absorptance of the subject for the light having the second wavelength. The pigment component identifying section 120 may use, as the second difference, the ratio between the intensity of the light having the first wavelength and the intensity of the light having the second wavelength, both of which are detected by the optical intensity detecting section 118.

The first absorptance may be calculated in advance based on the amount of the light having the first wavelength with which the subject is irradiated and the amount of the light having the first wavelength reflected by the subject. The pigment component identifying section 120 may obtain the first absorptance from a recording medium such as a memory that prestores the first absorptance.

The second absorptance may be calculated in advance based on the amount of the light having the second wavelength with which the subject is irradiated and the amount of the light having the second wavelength reflected by the subject. The pigment component identifying section 120 may obtain the second absorptance from a recording medium such as a memory that prestores the second absorptance.

The subject image obtaining section 126 obtains the subject image showing the subject. For example, the subject image obtaining section 126 obtains the subject image captured under the control performed by the image capturing control section 116. The subject image obtaining section 126 may obtain, as the subject image, an image containing a plurality of color components. For example, the subject image obtaining section 126 may obtain, as the subject image, a color image containing the R, G and B components.

The subject image obtaining section 126 may obtain the subject image containing a single color component. For example, the subject image obtaining section 126 may obtain, as the subject image, a black-and-white image containing the B component. The subject image obtaining section 126 may obtain, as the subject image, a black-and-white image containing the G component.

The subject image obtaining section 126 may obtain, as the subject image, an image based on the light having the first wavelength received by the light receiving section 114. For example, the subject image obtaining section 126 may obtain, as the subject image, an image based on light having a wavelength of 440 nm received by the light receiving section 114.

The subject image obtaining section 126 may obtain, as the subject image, an image based on the light having the second wavelength received by the light receiving section 114. For example, the subject image obtaining section 126 may obtain, as the subject image, an image based on light having a wavelength of 500 nm received by the light receiving section 114.

The illumination light component identifying section 122 identifies the illumination light component in the light from the subject, based on the subject image obtained by the subject image obtaining section 126 and the pigment component identified by the pigment component identifying section 120. The illumination light component identifying section 122 may identify the illumination light component in the light from the subject, by subtracting the color information of the pigment component identified by the pigment component identifying section 120 from the color information of the subject image obtained by the subject image obtaining section 126.

The illumination light component identifying section 122 may identify the illumination light component in the light from the subject, for each of the partial regions obtained by dividing the subject image. For example, the optical intensity detecting section 118 may detect, for each partial region, the intensity of the light having the first wavelength and the intensity of the light having the second wavelength. The pigment component identifying section 120 may identify, for each partial region, the pigment component in the light from the subject. The illumination light component identifying section 122 may identify, for each partial region, the illumination light component in the light from the subject. For example, the illumination light component identifying section 122 may identify the illumination light component in the light from the subject, in each partial region having 2×2, 4×4, or 8×8 pixels.

The pigment component enhancing section 128 enhances color information of the pigment component identified by the pigment component identifying section 120 in the subject image obtained by the subject image obtaining section 126. The pigment component enhancing section 128 may increase the intensity of the pigment component identified by the pigment component identifying section 120 in the subject image obtained by the subject image obtaining section 126. The pigment component enhancing section 128 may enhance the intensity of a single color component in the subject image obtained by the subject image obtaining section 126. For example, the pigment component enhancing section 128 may enhance the intensity of the G component in the subject image obtained by the subject image obtaining section 126.

The illumination light component enhancing section 130 enhances color information of the illumination light component identified by the illumination light component identifying section 122 in the subject image obtained by the subject image obtaining section 126. The illumination light component enhancing section 130 may increase the intensity of the illumination light component identified by the illumination light component identifying section 122 in the subject image obtained by the subject image obtaining section 126. The illumination light component enhancing section 130 may enhance the intensity of a single color component in the subject image obtained by the subject image obtaining section 126. For example, the illumination light component enhancing section 130 may enhance the intensity of the B component in the subject image obtained by the subject image obtaining section 126.

The illumination light image generating section 132 generates an image of the illumination light component identified by the illumination light component identifying section 122, by using the subject image obtained by the subject image obtaining section 126 and the pigment component identified by the pigment component identifying section 120. The illumination light image generating section 132 may generate the image of the illumination light component identified by the illumination light component identifying section 122, by subtracting the color information of the pigment component identified by the pigment component identifying section 120 from the color information of the subject image obtained by the subject image obtaining section 126.

The display section 134 displays a variety of images. For example, the display section 134 displays the subject image obtained by the subject image obtaining section 126. The display section 134 may display the image of the illumination light component generated by the illumination light image generating section 132. The display section 134 may achieve pseudo color display for the image of the illumination light component generated by the illumination light image generating section 132.

The display section 134 may display the subject image containing a plurality of color components. For example, the display section 134 may display the subject image containing the R, G and B components. The display section 134 may display the subject image containing a single color component. For example, the display section 134 may display the subject image containing the B component. Alternatively, the display section 134 may display the subject image containing the G component. The display section 134 may achieve pseudo color display for the subject image containing a single color component.

The display section 134 may display the subject image whose illumination light component is enhanced by the illumination light component enhancing section 130. The display section 134 may display the subject image whose pigment component is enhanced by the pigment component enhancing section 128. The display section 134 may switch the display between the subject image whose illumination light component is enhanced by the illumination light component enhancing section 130 and the subject image whose pigment component is enhanced by the pigment component enhancing section 128. The display section 134 may switch the display between the subject image obtained by the subject image obtaining section 126 and the image generated by the illumination light image generating section 132.

Figure 2:
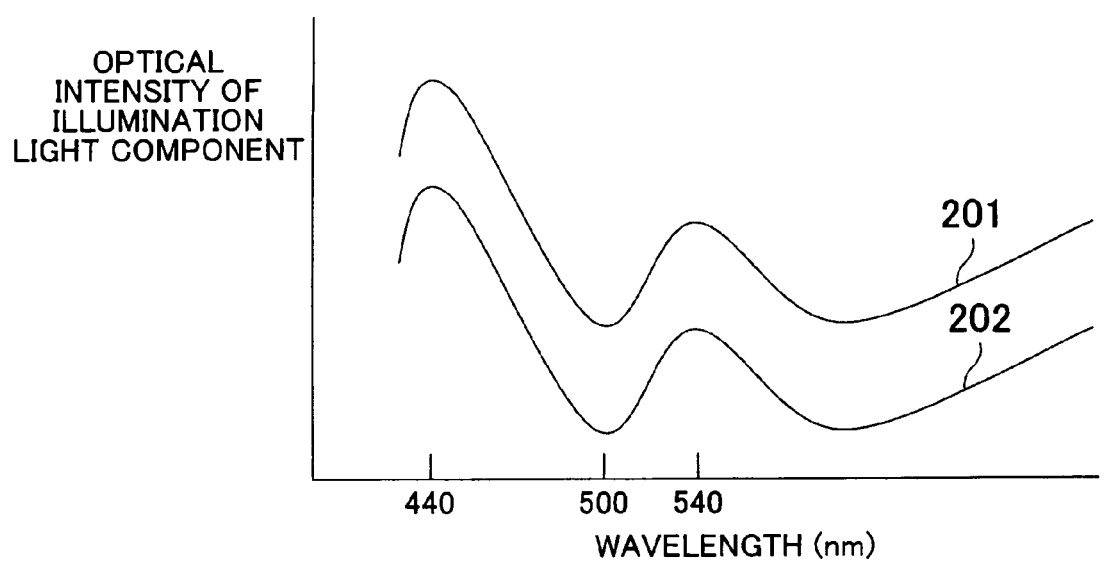
FIG. 2 illustrates exemplary frequency characteristics of an illumination light component in light from a subject.

FIG. 2 illustrates exemplary frequency characteristics of the illumination light component in the light from the subject. In the graph shown in FIG. 2, the horizontal axis represents the wavelength of the light, and the vertical axis represents the intensity of the illumination light component of the light from the subject. Frequency characteristics 201 and 202 each show the frequency characteristic of the illumination light component in the light from the subject. The frequency characteristics 201 and 202 are obtained by irradiating the subject with irradiation light having different intensities.

The frequency characteristics 201 and 202 each take a maximal value at the wavelength of 440 nm. Also, the frequency characteristics 201 and 202 each take a minimal value at the wavelength of 500 nm.

In other words, the frequency characteristics 201 and 202 indicate that the light absorption characteristic exhibits a minimal value at the wavelength of 440 nm for the illumination light component. Also, the frequency characteristics 201 and 202 indicate that the light absorption characteristic exhibits a maximal value at the wavelength of 500 nm for the illumination light component.

Here, the difference between the optical intensity shown by the frequency characteristic 201 and the optical intensity shown by the frequency characteristic 202 stays substantially constant at any wavelength. This means that the frequency characteristic of the illumination light component in the light from the subject does not vary depending on the intensity of the irradiation light with which the subject is irradiated. Therefore, when the first wavelength is set at 440 nm and the second wavelength is set at 500 nm, the difference in the optical intensity of the illumination light component in the light from the subject between the first wavelength and the second wavelength does not vary depending on the intensity of the irradiation light with which the subject is irradiated and thus remains substantially constant.

Figure 3:
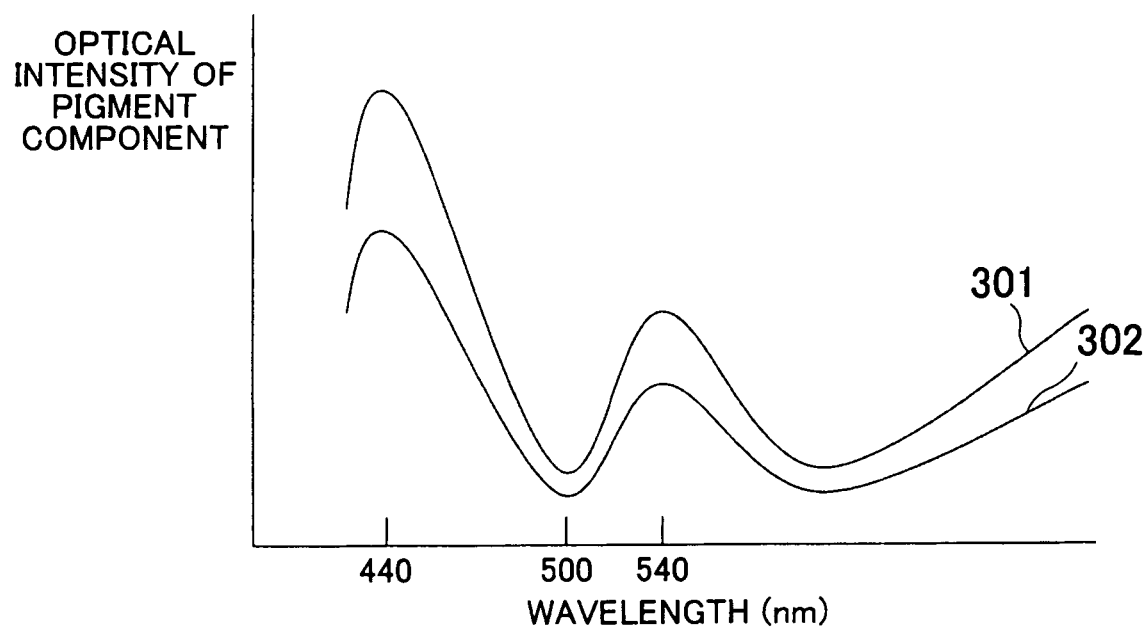
FIG. 3 illustrates exemplary frequency characteristics of a pigment component in the light from the subject.

FIG. 3 illustrates exemplary frequency characteristics of the pigment component in the light from the subject. In the graph shown in FIG. 3, the horizontal axis represents the wavelength of the light, and the vertical axis represents the optical intensity of the pigment component of the light from the subject. Frequency characteristics 301 and 302 each show the frequency characteristic of the pigment component in the light from the subject. The frequency characteristics 301 and 302 are obtained by irradiating the subject with irradiation light having different intensities.

The frequency characteristics 301 and 302 each take a maximal value at the wavelength of 440 nm, similarly to the frequency characteristics of the illumination light component in the light from the subject. Also, the frequency characteristics 301 and 302 each take a minimal value at the wavelength of 500 nm, similarly to the frequency characteristics of the illumination light component in the light from the subject.

In other words, the frequency characteristics 301 and 302 indicate that the light absorption characteristic exhibits a minimal value at the wavelength of 440 nm for the pigment component. Also, the frequency characteristics 301 and 302 indicate that the light absorption characteristic exhibits a maximal value at the wavelength of 500 nm for the pigment component.

Here, the difference between the optical intensity shown by the frequency characteristic 301 and the optical intensity shown by the frequency characteristic 302 varies depending on the wavelength. This means that the frequency characteristic of the pigment component in the light from the subject varies depending on the intensity of the irradiation light with which the subject is irradiated. Therefore, when the first wavelength is set at 440 nm and the second wavelength is set at 500 nm, the difference in the optical intensity of the pigment component in the light from the subject between the first wavelength and the second wavelength varies depending on the intensity of the irradiation light with which the subject is irradiated and thus is not constant.

As is apparent from FIGS. 2 and 3, the difference in absorptance between the first wavelength and the second wavelength, which may be referred to as a first difference, remains constant for the illumination light component and is variable for the pigment component. Considering this, the image capturing apparatus 100 relating to the present embodiment identifies the pigment component by referring to the difference between the first difference and a second difference, which denotes the difference in optical intensity of the light from the subject between the first wavelength and the second wavelength. The image capturing apparatus 100 then subtracts the identified pigment component from the subject image, thereby extracting the image of the illumination light component without influence of the pigment component of the subject.

Here, the first and second wavelengths may be set at 540 nm and 500 nm respectively. Alternatively, the first and second wavelengths may be set at 440 nm and 540 nm respectively. In these cases, the difference in absorptance between the first wavelength and the second wavelength also remains constant for the illumination light component and is variable for the pigment component. Therefore, the image capturing apparatus 100 can extract the image of the illumination light component from the subject image in a similar manner as in the case where the first and second wavelengths are set at 440 nm and 500 nm respectively.

Figure 4:
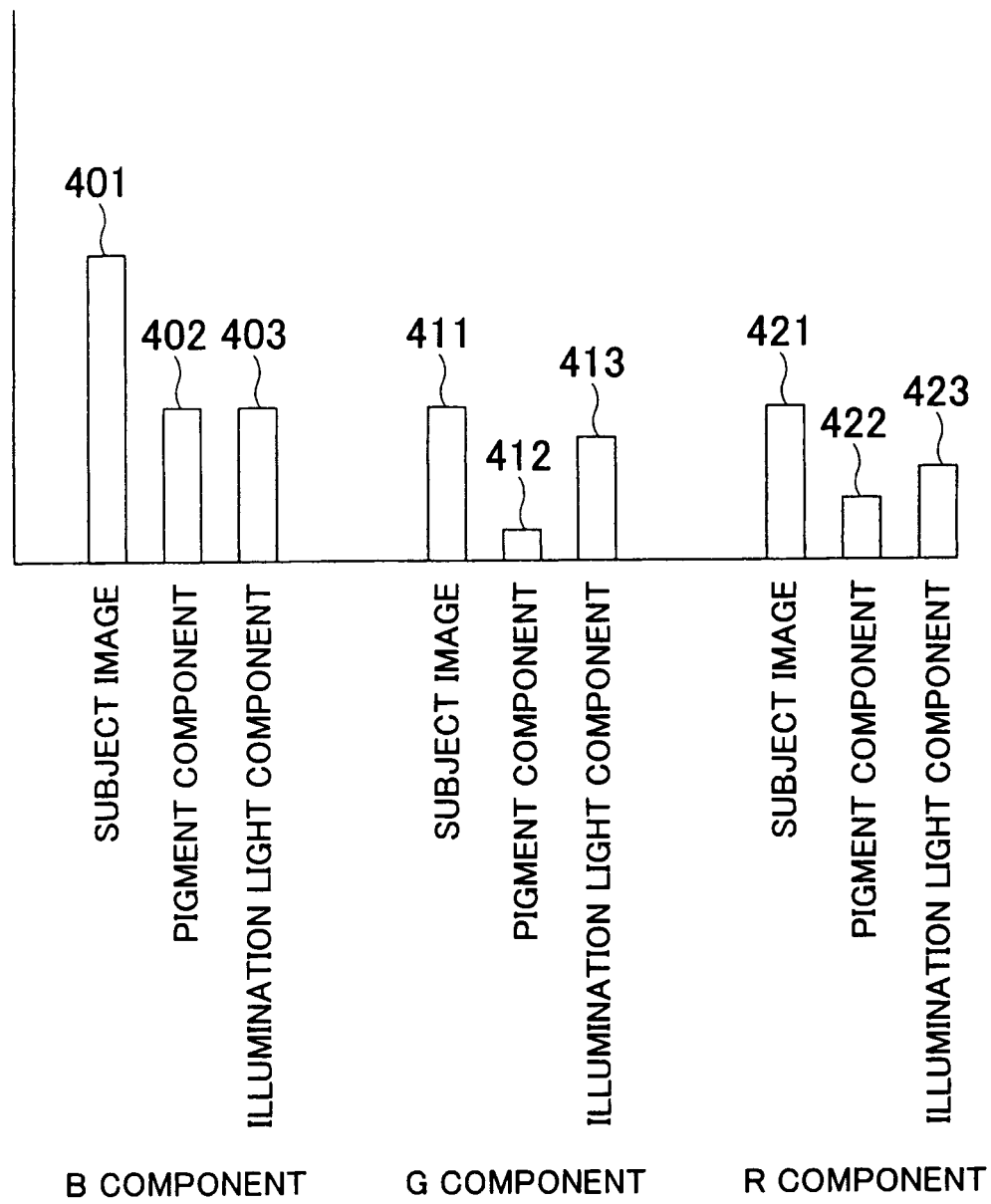
FIG. 4 illustrates exemplary color components contained in a subject image obtained by a subject image obtaining section 126.

FIG. 4 illustrates exemplary color components contained in the subject image obtained by the subject image obtaining section 126. In FIG. 4, intensities designated by the reference numerals 401, 411 and 421 are the intensities of the respective color components in the subject image obtained by the subject image obtaining section 126.

The intensity 401 is the intensity of the B component (420 nm to 490 nm) in the subject image. The intensity 411 is the intensity of the G component (490 nm to 600 nm) in the subject image. The intensity 421 is the intensity of the R component (600 nm to 750 nm) in the subject image.

Intensities designated by the reference numerals 402, 412 and 422 are the intensities of the respective color components in the pigment component of the subject image, which is identified by the pigment component identifying section 120. The intensity 402 is the intensity of the B component (420 nm to 490 nm) in the pigment component of the subject image. The intensity 412 is the intensity of the G component (490 nm to 600 nm) in the pigment component of the subject image. The intensity 422 is the intensity of the R component (600 nm to 750 nm) in the pigment component of the subject image. For example, the pigment component identifying section 120 can identify the intensities 402, 412, and 422, based on the color information stored on the subject information storing section 124.

In one example, the pigment component identifying section 120 first obtains the difference in the absorptance of the subject between the wavelength of 440 nm and the wavelength of 500 nm, that is to say, the first difference. Specifically speaking, the pigment component identifying section 120 obtains the first difference from a memory or the like that stores thereon the first difference. After this, the pigment component identifying section 120 calculates the difference in the optical intensity detected by the optical intensity detecting section 118 between the wavelength of the 440 nm and the wavelength of the 500 nm, that is to say, the second difference.

Subsequently, the pigment component identifying section 120 obtains from the subject information storing section 124 the color information associated with the obtained first difference and the calculated second difference. For example, the color information obtained from the subject information storing section 124 indicates the intensities of the B, G and R components. Thus, the pigment component identifying section 120 can identify the intensities 402, 412, and 422, based on the color information stored on the subject information storing section 124.

According to a different example, the pigment component identifying section 120 first obtains the difference in the absorptance of the subject between the wavelength of 440 nm and the wavelength of 500 nm, that is to say, the first difference. Specifically speaking, the pigment component identifying section 120 obtains the first difference from a memory or the like that stores thereon the first difference. After this, the pigment component identifying section 120 calculates the difference in optical intensity detected by the optical intensity detecting section 118 between the wavelength of 440 nm and the wavelength of 500 nm, that is to say, the second difference.

Subsequently, the pigment component identifying section 120 calculates a difference between the obtained first difference and the calculated second difference. The pigment component identifying section 120 obtains from the subject information storing section 124 the color information associated with the calculated difference. For example, the color information obtained from the subject information storing section 124 indicates the intensities of the B, G and R components. Thus, the pigment component identifying section 120 can identify the intensities 402, 412, and 422, based on the color information stored on the subject information storing section 124.

The pigment component identifying section 120 may identify the intensities 402, 412, and 422, for each of the pixels of the subject image. Alternatively, the pigment component identifying section 120 may identify the intensities 402, 412, and 422, for each of the partial regions of the subject image. For example, the pigment component identifying section 120 may identify the intensities 402, 412, and 422, for each of the partial regions formed by 4×4, 8×8, or 16×16 pixels in the subject image.

Intensities designated by the reference numerals 403, 413 and 423 are the intensities of the respective color components of the illumination light component in the subject image, which is identified by the illumination light component identifying section 122. The intensity 403 is the intensity of the B component (420 nm to 490 nm) in the illumination light component of the subject image. The intensity 413 is the intensity of the G component (490 nm to 600 nm) in the illumination light component of the subject image. The intensity 423 is the intensity of the R component (600 nm to 750 nm) in the illumination light component of the subject image.

For example, the illumination light component identifying section 122 may calculate the intensity 403 of the B component in the illumination light component of the subject image, by subtracting the intensity 402 of the B component in the pigment component of the subject image from the intensity 401 of the B component in the subject image. The illumination light component identifying section 122 may calculate the intensity 413 of the G component in the illumination light component of the subject image, by subtracting the intensity 412 of the G component in the pigment component of the subject image from the intensity 411 of the G component in the subject image. The illumination light component identifying section 122 may calculate the intensity 423 of the R component in the illumination light component of the subject image, by subtracting the intensity 422 of the R component in the pigment component of the subject image from the intensity 421 of the R component in the subject image.

The illumination light component identifying section 122 may identify the intensities 403, 413, and 423, for each of the pixels of the subject image. Alternatively, the illumination light component identifying section 122 may identify the intensities 403, 413, and 423, for each of the partial regions of the subject image. For example, the illumination light component identifying section 122 may identify the intensities 403, 413, and 423, for each of the partial regions formed by 4×4, 8×8, or 16×16 pixels in the subject image.

Figure 5:
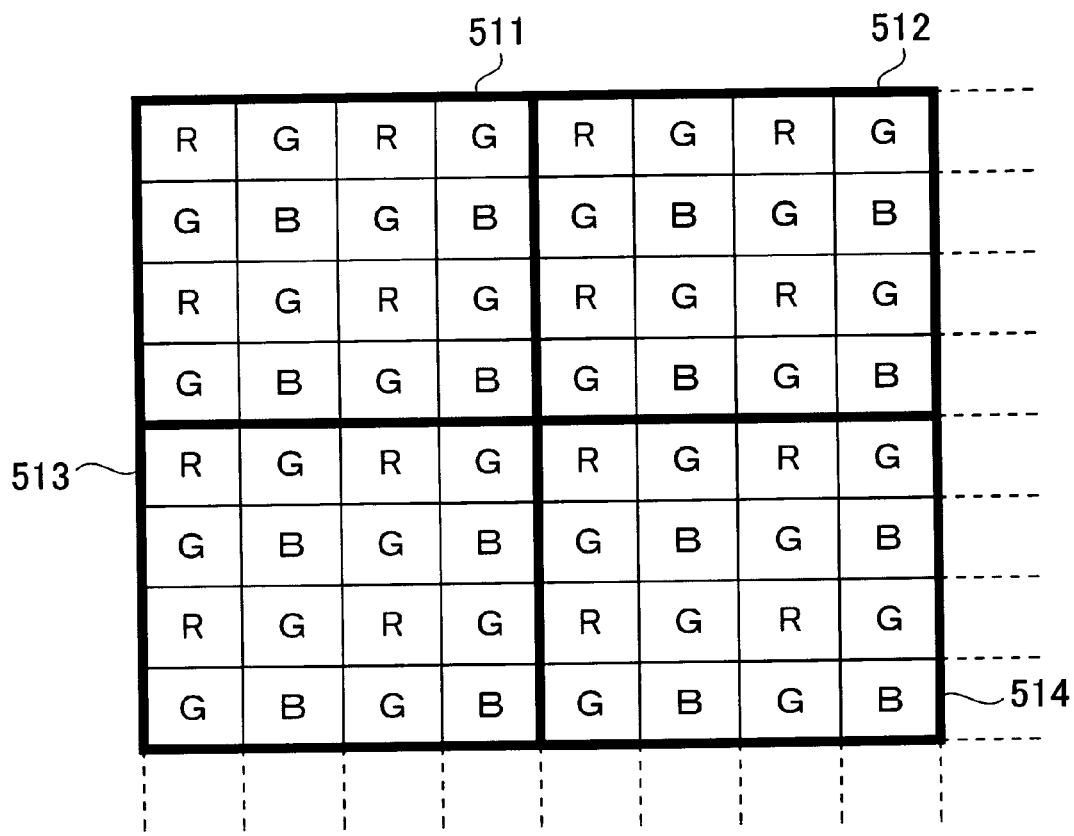
FIG. 5 illustrates exemplary partial regions, in each of which the pigment component and the illumination light component are identified.

FIG. 5 illustrates exemplary partial regions, in each of which the pigment component and the illumination light component are identified. FIG. 5 shows the subject image obtained by the subject image obtaining section 126. An image 500 includes partial regions 511, 512, 513 and 514. Each partial region includes 4×4 pixels.

The pixel arrangement of the image 500 is merely an example of how to arrange the R, G and B components, and the present invention is not limited to such. The number of pixels in each partial region is not limited to 4×4, and can be 8×8 or 16×16.

The pigment component identifying section 120 may identify the pigment component in each of the partial regions 511, 512, 513 and 514. For example, the pigment component identifying section 120 may identify the intensities of the R, G and B components of the pigment component, in each of the partial regions 511, 512, 513 and 514.

The illumination light component identifying section 122 may identify the illumination light component in each of the partial regions 511, 512, 513 and 514. For example, the illumination light component identifying section 122 may identify the intensities of the R, G and B components of the illumination light component, in each of the partial regions 511, 512, 513 and 514.

FIG. 6 illustrates an example of the subject image obtained by the subject image obtaining section 126. A subject image 600 shows a protrusion portion 601, an influenced region 602 and an influenced region 603.

In the subject image 600, the protrusion portion 601 is positioned in a relatively bright region. Therefore, an observer such as a medical doctor can refer to the subject image 600 to accurately diagnose the condition of the protrusion portion 601. In the subject image 600, on the other hand, the influenced regions 602 and 603 are positioned in a relatively dark region, and darkened under the influence of the pigment of the subject. Therefore, an observer such as a medical doctor cannot refer to the subject image 600 to accurately diagnose the condition of the surface of the subject in the influenced portions 602 and 603.

Figure 7:
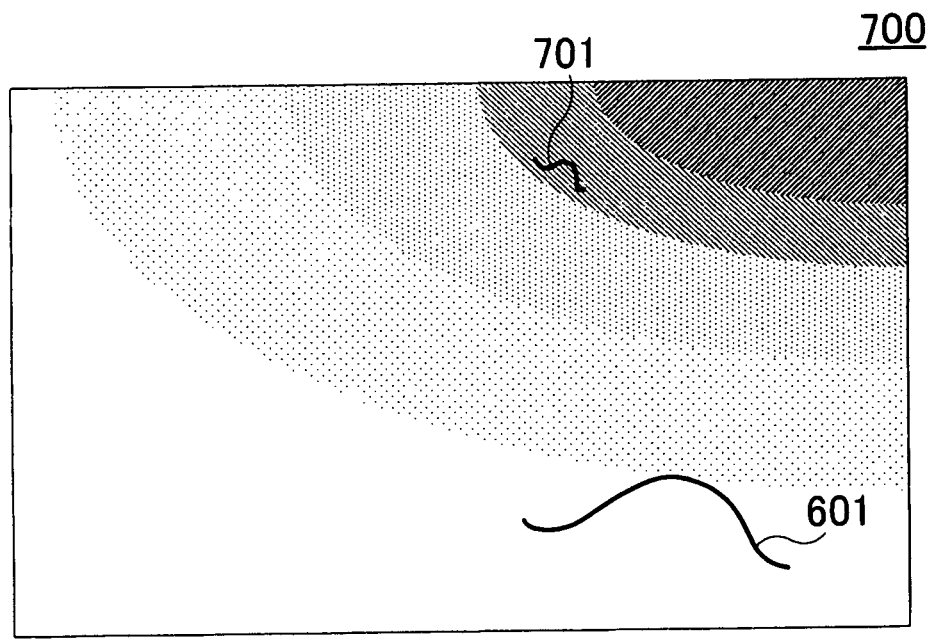
FIG. 7 illustrates an example of an image generated by an illumination light image generating section 132.

FIG. 7 illustrates an example of the image generated by the illumination light image generating section 132. An image 700 is of the illumination light component, and is generated by subtracting the color information of the pigment component identified by the pigment component identifying section 120 from the color information of the subject image 600 shown in FIG. 6.

Since the color information of the pigment component has been subtracted, the image 700 no longer includes the influenced regions 602 and 603, which are present in the subject image 600. Therefore, the image 700 visibly shows a protrusion portion 701. As a consequence, an observer such as a medical doctor can refer to the image 700 to accurately diagnose the condition of the protrusion 701.

Figure 8:
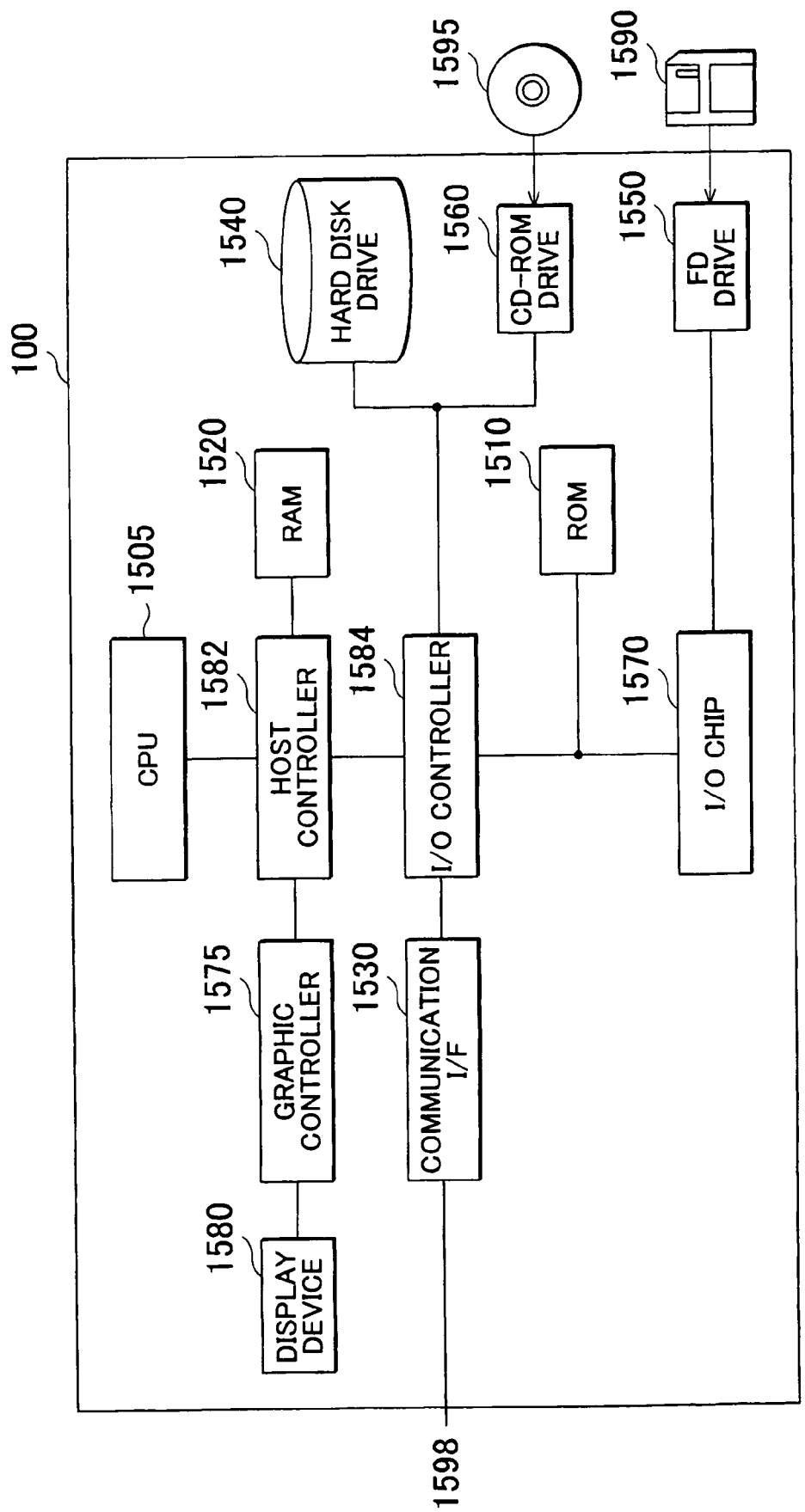
FIG. 8 illustrates an exemplary hardware configuration of the image capturing apparatus 100.

FIG. 8 illustrates an exemplary hardware configuration of the image capturing apparatus 100. The image capturing apparatus 100 is constituted by a CPU surrounding section, an input/output (I/O) section and a legacy I/O section. The CPU surrounding section includes a CPU 1505, a RAM 1520, a graphic controller 1575, and a display device 1580 which are connected to each other by means of a host controller 1582. The I/O section includes a communication interface 1530, a hard disk drive 1540, and a CD-ROM drive 1560 which are connected to the host controller 1582 by means of an I/O controller 1584. The legacy I/O section includes a ROM 1510, a flexible disk drive 1550, and an I/O chip 1570 which are connected to the I/O controller 1584.

The host controller 1582 connects the RAM 1520 with the CPU 1505 and graphic controller 1575 which access the RAM 1520. The CPU 1505 operates in accordance with programs stored on the ROM 1510 and RAM 1520, to control the constituents. The graphic controller 1575 obtains image data which is generated by the CPU 1505 or the like on a frame buffer provided within the RAM 1520, and causes the display device 1580 to display the obtained image data. Alternatively, the graphic controller 1575 may include therein a frame buffer for storing thereon image data generated by the CPU 1505 or the like.

The I/O controller 1584 connects, to the host controller 1582, the hard disk drive 1540, communication interface 1530 and CD-ROM drive 1560 which are I/O devices operating at a relatively high rate. The hard disk drive 1540 stores thereon programs and data to be used by the CPU 1505. The communication interface 1530 couples to the network communication apparatus 1598, to transmit/receive programs or data. The CD-ROM drive 1560 reads programs or data from a CD-ROM 1595, and supplies the read programs or data to the hard disk drive 1540 and communication interface 1530 via the RAM 1520.

The I/O controller 1584 is also connected to the ROM 1510, flexible disk drive 1550 and I/O chip 1570 which are I/O devices operating at a relatively low rate. The ROM 1510 stores thereon a boot program executed by the image capturing apparatus 100 at the start up, programs dependent on the hardware of the image capturing apparatus 100 and the like. The flexible disk drive 1550 reads programs or data from a flexible disk 1590, and supplies the read programs or data to the hard disk drive 1540 and communication interface 1530 via the RAM 1520. The I/O chip 1570 is used to connect a variety of I/O devices such as the flexible disk drive 1550 via, for example, a parallel port, a serial port, a keyboard port, a mouse port or the like.

The program to be executed by the CPU 1505 is provided by a user in the state of being stored on a recording medium such as the flexible disk 1590, the CD-ROM 1595, and an IC card. The program may be stored on the recording medium in the state of being compressed or not being compressed. The program is installed from the recording medium onto the hard disk drive 1540, read by the RAM 1520, and executed by the CPU 1505. The program executed by the CPU 1505 causes the image capturing apparatus 100 to function as the respective constituents of the image capturing apparatus 100 described with reference to FIGS. 1 to 7.

The program mentioned above may be stored on an external recording medium. The recording medium is, for example, an optical recording medium such as DVD and PD, a magnet-optical recording medium such as MD, a tape medium, a semiconductor memory such as an IC card and the like, in addition to the flexible disk 1590 and CD-ROM 1595. The recording medium may be a storage device such as a hard disk or RAM which is provided in a server system connected to a dedicated communication network or the Internet, and the program may be provided to the image capturing apparatus 100 via the network.

Although some aspects of the present invention have been described by way of exemplary embodiments, it should be understood that those skilled in the art might make many changes and substitutions without departing from the spirit and the scope of the present invention which is defined only by the appended claims.

The claims, specification and drawings describe the processes of an apparatus, a system, a program and a method by using the terms such as operations, procedures, steps and stages. When a reference is made to the execution order of the processes, wording such as "before" or "prior to" is not explicitly used. The processes may be performed in any order unless an output of a particular process is used by the following process. In the claims, specification and drawings, a flow of operations may be explained by using the terms such as "first" and "next" for the sake of convenience. This, however, does not necessarily indicate that the operations should be performed in the explained order.

What is claimed is:

1. A signal processing apparatus for separating light from a specified subject into an illumination light component and a pigment component, the illumination light component resulting from a color of light with which the subject is irradiated, the pigment component resulting from a color of a pigment of the subject, the signal processing apparatus comprising a processor, the processor including a program stored therein for causing the processor to perform executable sections, the executable sections comprising:

a subject image obtaining section that obtains a subject image including R, G, and B components;

an optical intensity detecting section that detects an intensity of the light from the subject at a first wavelength and a second wavelength, the first wavelength being different from the second wavelength;

a pigment component identifying section that identifies the pigment component of the subject image, based on a difference between a first absorptance of the subject at the first wavelength and a second absorptance of the subject at the second wavelength, and a difference between an intensity at the first wavelength and an intensity at the second wavelength that are detected by the optical intensity detecting section;

an illumination light component identifying section that identifies the illumination light component of the subject image, based on the subject image and the pigment component identified by the pigment component identifying section, wherein the optical intensity detecting section detects the intensity of the light from the subject at the first wavelength, at which a light absorption characteristic of the subject takes a minimal value and at the second wavelength, at which the light absorption characteristic of the subject takes a maximal value;

a subject information storing section that stores color information of the subject indicating intensities of respective R, G and B components in association with the difference between the first absorptance and the second absorptance of the subject and the difference between the detected intensity at the first wavelength and the detected intensity at the second wavelength, wherein the pigment component identifying section identifies intensities for respective R, G and B components of the pigment component of the subject image, based on the color information stored in the subject information storing section, and wherein the illumination light component identifying section identifies intensities for respective R, G and B components of the illumination light component of the subject image, by subtracting intensities for respective R, G, and B components of the pigment component identified by the pigment component identifying section from intensities for respective R, G, and B components of color information of the subject image; and an illumination light image generating section that generates an image of the illumination light component identified by the illumination light component identifying section, by subtracting color information of the pigment component identified by the pigment component identifying section from the color information of the subject image obtained by image-capturing the subject.

2. The signal processing apparatus as set forth in claim 1, wherein the optical intensity detecting section detects the intensity of the light from the subject at the first and second wavelengths in each of partial regions obtained by dividing the subject image, wherein the pigment component identifying section identifies the pigment component of the subject image in each of the partial regions, and wherein the illumination light component identifying section identifies the illumination light component of the subject image in each of the partial regions.

3. The signal processing apparatus as set forth in claim 2, further comprising:

an illumination light component enhancing section that enhances, in the subject image obtained by image-capturing the subject, color information of the illumination light component identified by the illumination light component identifying section.

4. The signal processing apparatus as set forth in claim 2, further comprising:
a pigment component enhancing section that enhances, in the subject image obtained by image-capturing the subject, color information of the pigment component identified by the pigment component identifying section.

5. The signal processing apparatus as set forth in claim 1, wherein, in said signal processing apparatus, the intensity of the light from the subject increases prior to the first wavelength that the light absorption characteristic of the subject takes the minimal value, and
wherein, in said signal processing apparatus, the intensity of the light from the subject decreases after the second wavelength that the light absorption characteristic of the subject takes the minimal value.

6. The signal processing apparatus as set forth in claim 5, wherein, in said signal processing apparatus, the intensity of the light from the subject decreases prior to the first wavelength that the light absorption characteristic of the subject takes the maximal value, and
wherein, in said signal processing apparatus, the intensity of the light from the subject increases after the second wavelength that the light absorption characteristic of the subject takes the maximal value.

7. The signal processing apparatus as set forth in claim 1, wherein, in said signal processing apparatus, a frequency characteristic of the illumination light component of the subject image is independent of an intensity of irradiation light with which the subject is irradiated.

8. The signal processing apparatus as set forth in claim 1, wherein, in said signal processing apparatus, the difference between the first absorptance of the subject at the first wavelength and the second absorptance of the subject at the second wavelength is constant for the illumination light component.

9. The signal processing apparatus as set forth in claim 8, wherein, in said signal processing apparatus, the difference between the first absorptance of the subject at the first wavelength and the second absorptance of the subject at the second wavelength is variable for the pigment component.

10. The signal processing apparatus as set forth in claim 1, wherein, in said signal processing apparatus, the intensity of the light from the subject changes before and after the first wavelength and the second wavelength.

11. A signal processing method for separating light from a specified subject into an illumination light component and a pigment component, the illumination light component resulting from a color of light with which the subject is irradiated, the pigment component resulting from a color of a pigment of the subject, the signal processing method comprising:
obtaining a subject image including R, G, and B components;
detecting an intensity of the light from the subject at a first wavelength and a second wavelength, the first wavelength being different from the second wavelength;
identifying the pigment component of the subject image, based on a difference between a first absorptance of the subject at the first wavelength and a second absorptance of the subject at the second wavelength, and a difference between an intensity at the first wavelength and an intensity at the second wavelength that are detected in the intensity detecting;
identifying the illumination light component of the subject image, based on the subject image and the pigment component identified in the pigment component identifying,
wherein said detecting comprises detecting the intensity of the light from the subject at the first wavelength, at which a light absorption characteristic of the subject takes a minimal value and at the second wavelength, at which the light absorption characteristic of the subject takes a maximal value;
storing color information of the subject indicating intensities of respective R, G and B components in association with the difference between the first absorptance and the second absorptance of the subject and the difference between the detected intensity at the first wavelength and the detected intensity at the second wavelength,
wherein the identifying the illumination light component comprises identifying intensities for respective R, G and B components of the pigment component of the subject image, based on the color information stored in the storing color information, and
wherein, said identifying the illumination light component comprises identifying intensities for respective R, G and B components of the illumination light component of the subject image, by subtracting intensities for respective R, G, and B components of the identified pigment component from intensities for respective R, G, and B components of color information of the subject image; and
generating, by a processor of a computer, an image of the identified illumination light component by subtracting color information of the identified pigment component from the color information of the subject image.

12. The signal processing method as set forth in claim 11, wherein the intensity of the light from the subject changes before and after the first wavelength and the second wavelength.

13. A non-transitory computer readable medium storing thereon a program for use with a signal processing apparatus that separates light from a specified subject into an illumination light component and a pigment component, the illumination light component resulting from a color of light with which the subject is irradiated, the pigment component resulting from a color of a pigment of the subject, the program causing a computer to perform functions in executable sections, the executable sections comprising:
a subject image obtaining section that obtains a subject image including R, G, and B components;
an optical intensity detecting section that detects an intensity of the light from the subject at a first wavelength and a second wavelength, the first wavelength being different from the second wavelength;
a pigment component identifying section that identifies the pigment component of the subject image, based on a difference between a first absorptance of the subject at the first wavelength and a second absorptance of the subject at the second wavelength, and a difference between an intensity at the first wavelength and an intensity at the second wavelength that are detected by the optical intensity detecting section;
an illumination light component identifying section that identifies the illumination light component of the subject image, based on the subject image and the pigment component identified by the pigment component identifying section,
wherein the optical intensity detecting section detects the intensity of the light from the subject at the first wavelength, at which a light absorption characteristic of the subject takes a minimal value and at the second wavelength, at which the light absorption characteristic of the subject takes a maximal value;
a subject information storing section that stores color information of the subject indicating intensities of respective R, G and B components in association with the difference between the first absorptance and the second absorptance of the subject and the difference between the detected intensity at the first wavelength and the detected intensity at the second wavelength,
   wherein the pigment component identifying section identifies intensities for respective R, G and B components of the pigment component of the subject image, based on the color information stored in the subject information storing section, and
   wherein the illumination light component identifying section identifies intensities for respective R, G and B components of the illumination light component of the subject image, by subtracting intensities for respective R, G, and B components of the pigment component identified by the pigment component identifying section from intensities for respective R, G, and B components of color information of the subject image; and
an illumination light image generating section that generates an image of the illumination light component identified by the illumination light component identifying section, by subtracting color information of the pigment component identified by the pigment component identifying section from the color information of the subject image obtained by image-capturing the subject.

14. The non-transitory computer readable medium as set forth in claim 13, wherein, in said signal processing apparatus, the intensity of the light from the subject changes before and after the first wavelength and the second wavelength.

* * * * *